(12) United States Patent
Kim et al.

(10) Patent No.: US 9,545,363 B2
(45) Date of Patent: Jan. 17, 2017

(54) MACHINABLE ZIRCONIA COMPRISING TITANIA NANOPOWDER

(71) Applicant: ACUCERA INC., Namyangju-si, Gyeonggi-do (KR)

(72) Inventors: Dae-Joon Kim, Seoul (KR); Sang Wook Kim, Seoul (KR); Seung Won Seo, Anyang-si (KR); Yong Hwan Jeong, Namyangju-si (KR)

(73) Assignee: ACUCERA INC., Namyangju-si, Gyeonggi-do (KR)

(*) Notice: Subject to any disclaimer, the term of this patent is extended or adjusted under 35 U.S.C. 154(b) by 1 day.

(21) Appl. No.: 14/581,900

(22) Filed: Dec. 23, 2014

(65) Prior Publication Data

US 2015/0183690 A1    Jul. 2, 2015

(30) Foreign Application Priority Data

Dec. 27, 2013  (KR) .................... 10-2013-0166242

(51) Int. Cl.
*C04B 35/49* (2006.01)
*A61K 6/02* (2006.01)
(Continued)

(52) U.S. Cl.
CPC ............. *A61K 6/024* (2013.01); *C04B 35/486* (2013.01); *C04B 35/49* (2013.01);
(Continued)

(58) Field of Classification Search
CPC ...... C04B 35/49; C04B 35/495; C04B 35/505; C04B 35/6455
(Continued)

(56) References Cited

U.S. PATENT DOCUMENTS 5,502,012 A * 3/1996 Bert .................. B02C 17/20
                                                501/103
5,863,850 A * 1/1999 Nawa ................ C04B 35/119
                                                501/103
(Continued)

FOREIGN PATENT DOCUMENTS

JP    1-290558 A    11/1989
JP    3-237060 A    10/1991
(Continued)

OTHER PUBLICATIONS

Trunec, Effect of Grain Size on Mechanical Properties of 3Y-TZP Ceramics, Department of Ceramics and Polymers, Brno University of Technology, Brno, Czech Republic, Sep. 2008.*

(Continued)

*Primary Examiner* — Holly Le
(74) *Attorney, Agent, or Firm* — Harness, Dickey & Pierce, P.L.C.

(57) ABSTRACT

Provided is a machinable zirconia having high translucency as a sintered body which is formed to include a tetragonal zirconia composite powder containing 79.8 to 92 mol % $ZrO_2$, 4.5 to 10.2 mol % $Y_2O_3$, 3.5 to 7.5 mol % $Nb_2O_5$ or 5.5 to 10.0 mol % $Ta_2O_5$, and a $TiO_2$ nano powder which is added with a weight ratio of more than 0 wt % and up to 2.5 wt % to the composite powder, wherein a density of the sintered body is 99% or more, an average grain size of the sintered body is 2 μm or larger, hardness of the sintered body is in a range of 4 to 10 GPa, fracture toughness of the sintered body is in a range of 9 to 14 MPa·m$^{1/2}$, a strength of the sintered body is in a range of 400 to 1000 MPa.

8 Claims, 12 Drawing Sheets
(2 of 12 Drawing Sheet(s) Filed in Color)

(51) Int. Cl.
*C04B 35/645* (2006.01)
*C04B 35/626* (2006.01)
*C04B 35/64* (2006.01)
*C04B 35/486* (2006.01)

(52) U.S. Cl.
CPC .. *C04B 35/62655* (2013.01); *C04B 35/62695* (2013.01); *C04B 35/64* (2013.01); *C04B 35/6455* (2013.01); C04B 2235/3224 (2013.01); *C04B 2235/3225* (2013.01); C04B 2235/3229 (2013.01); C04B 2235/3232 (2013.01); C04B 2235/3251 (2013.01); C04B 2235/3418 (2013.01); *C04B 2235/5436* (2013.01); *C04B 2235/5454* (2013.01); C04B 2235/608 (2013.01); C04B 2235/6567 (2013.01); C04B 2235/661 (2013.01); C04B 2235/765 (2013.01); C04B 2235/77 (2013.01); C04B 2235/9653 (2013.01); *Y10T 428/2982* (2015.01)

(58) Field of Classification Search
USPC ......... 501/103, 134, 153, 152; 264/460, 681
See application file for complete search history.

(56) References Cited

U.S. PATENT DOCUMENTS

| | | | |
|---|---|---|---|
| 6,380,113 B1* | 4/2002 | Kim | C04B 35/4885 264/664 |
| 7,700,508 B1 | 4/2010 | Zhu | |
| 2010/0012484 A1 | 1/2010 | Citti | |
| 2011/0254181 A1* | 10/2011 | Holand | A61K 6/0008 264/6 |
| 2012/0058883 A1* | 3/2012 | Yamashita | C04B 35/49 501/134 |
| 2013/0011610 A1* | 1/2013 | Stephan | C04B 41/515 428/141 |

FOREIGN PATENT DOCUMENTS

| | | |
|---|---|---|
| JP | 8-117248 A | 5/1996 |
| JP | 2000-191372 A | 7/2000 |
| JP | 2008-222450 A | 9/2008 |
| KR | 10-0840777 B1 | 6/2008 |

OTHER PUBLICATIONS

Database WPI, Week 200903, Thomson Scientific, London, GB; AN 2009-A65234 XP002737081, & KR 100 840 77 B1 (Acucera Inc) Jun. 23, 2008 (Jun. 23, 2008), *Abstract; Claim 2; figure 4; table 1; example 1*.
European Search Report in corresponding with European Application No. 14199959.9-1354 dated Mar. 20, 2015.

\* cited by examiner

MACHINABLE ZIRCONIA

MACHINABLE ZIRCONIA

MACHINABLE ZIRCONIA COMPRISING TITANIA NANOPOWDER

CROSS REFERENCES TO RELATED APPLICATIONS

The present invention contains subject matter related to Korean Patent Application No. 10-2103-0166242, filed in the Korean Patent Office on Dec. 27, 2013, the entire contents of which are incorporated herein by reference.

BACKGROUND OF THE INVENTION

Field of the Invention

The present invention relates to a machinable zirconia, and more particularly, to a zirconia having excellent strength and fracture toughness, low hardness, and high translucency so as to have excellent machinability.

Description of the Related Art

Up to now, the field of dental restorations has been remarkably grown.

In the related art, as a material for artificial teeth substituting for natural teeth, metals have been mainly used. However, recently, prostheses made of ceramics having excellent beauty and having color similar to those of natural teeth have been widely used. As a ceramic material for dental products, zirconia has no inferiority as a substitute for metal prostheses or other ceramic materials in terms of strength and beauty. The zirconia has chemical resistance, abrasion resistance, and a high melting point. Therefore, the zirconia is a material which has attracted much attention in various industrial fields beside the dental field. In addition, since the zirconia is a material which is free from cytotoxicity, carcinogens, heavy metals, and the like, the zirconia has been favored as a ceramic for biological structures.

Recently, a prosthesis is manufactured by using the zirconia in a CAD/CAM manufacturing method (design and manufacturing method utilizing a computer) instead of a prosthesis manufacturing method of the related art. In the CAD/CAM manufacturing method, after a state of the mouth is directly scanned, or a mold for manufacturing a prosthesis is scanned without a process of casting a dental mold as a general process, a form of teeth is designed by using a CAD program, and the prosthesis is manufactured. Based on virtual teeth completed by using the CAD program on a computer, the zirconia is machined by a dedicated milling machine, so that actual teeth suitable for a patient are completed.

However, the zirconia used as a material for dental products has a disadvantage in that machining is hard to perform because of high hardness although mechanical properties are excellent. Because of this problem, before a sintered body is finally completed, a porous zirconia is manufactured through primary sintering at a low temperature, and after that, a machining step is performed, and secondary sintering is performed, so that the prosthesis is completed. By taking into consideration shrinkage of the porous zirconia during the final sintering process, the prosthesis needs to be formed with a volume which is larger about 20% or more.

As described above, since the zirconia has a problem in that the machinability is deteriorated, much time and cost are spent on manufacturing the prostheses for artificial teeth. In addition, since it is difficult to machine the final shape of the prostheses as an optimized structure for the patient's mouth, there is a limitation to increase competitiveness of the zirconia prostheses.

SUMMARY OF THE INVENTION

The present invention is to provide a zirconia having enhanced machinability.

The present invention is also to provide a zirconia for artificial teeth which has excellent machinability and strength and translucency.

The present invention is also to provide a fully sintered zirconia having beauty used for recovering teeth in a real-time CAD/CAM method, which has good fitness to removed teeth without a post machining process by omitting consideration of a secondary full sintering process after machining and a shrinking ratio thereof which is a disadvantage of a half sintered zirconia of the related art.

Other objects and technical characteristics of the present invention will be disclosed more in detail in the following detailed description.

According to an aspect of the present invention, there is provided a machinable zirconia as a sintered body which is formed to include a tetragonal zirconia composite powder containing 79.8 to 92 mol % $ZrO_2$, 4.5 to 10.2 mol % $Y_2O_3$, and 3.5 to 7.5 mol % $Nb_2O_5$, or 5.5 to 10.0 mol % $Ta_2O_5$ and a $TiO_2$ nano powder which is added with a weight ratio of more than 0 wt % and up to 2.5 wt % to the composite powder, wherein a density of the sintered body is 99% or more, an average particle diameter of particles of the sintered body is 2 μm or more, hardness of the sintered body is in a range of 4 to 10 GPa, fracture toughness of the sintered body is in a range of 9 to 14 $MPa \cdot m^{1/2}$, a strength of the sintered body is in a range of 400 to 1000 MPa.

In the above aspect, the sintered body may further contain $CeO_2$ in a range of 0.5 to 3 wt %, and the sintered body may further contain $SiO_2$ in a range of 0.2 to 0.8 wt %.

According to another aspect of the present invention, there is provided a method of manufacturing a machinable zirconia, including preparing a raw material including a tetragonal zirconia composite powder containing 79.8 to 92 mol % $ZrO_2$, 4.5 to 10.2 mol % $Y_2O_3$, and 3.5 to 7.5 mol % $Nb_2O_5$, or 5.5 to 10.0 mol % $Ta_2O_5$ and a $TiO_2$ nano powder which is added with a weight ratio of more than 0 wt % and up to 2.5 wt % to the composite powder, forming composite granules by spraying and drying slurry containing the raw material, and performing sintering after molding the granules, wherein the sintering is performed at a temperature range of 1500 to 1700° C. for 2 to 40 hours followed by hot isostatic press (HIP) at temperature range of 1400 to 1700° C. for 0.1 to 10 hrs.

In the above aspect, the sintering may include increasing the temperature up to a temperature of 1400 to 1600° C., retaining the temperature for a predetermined time, and increasing the temperature up to a temperature of 1500 to 1700° C., and the retaining the temperature may be performed in a temperature range of 1300 to 1500° C. for 20 to 30 hours.

In addition, after the sintering, HIP may be additionally performed in a temperature range of 1300 to 1700° C. with a pressure of 10000 to 50000 psi so as to improve physical properties.

According to the present invention, it is possible to decrease hardness of a zirconia while maintaining high strength and high fracture toughness, so that it is possible to obtain excellent machinability. In addition, it is possible to obtain excellent translucency and color similar to that of teeth, and it is possible to prevent a deterioration caused by phase transition even in the case of low temperature thermal treatment. Therefore, the machinable zirconia according to the present invention can be effectively applied to a molded product for biological transplantation, particularly, a dental prosthesis. In particular, according to the present invention, it is possible to provide a machinable zirconia block which can be used in a real-time CAD/CAM system. Since a fully sintered zirconia of the related art has high hardness, products are manufactured in a half sintered state depending on a CAD/CAM device in a dental factory, and thus, there is a problem in that the production cost is high. According to the present invention, this problem is solved, so that it is possible to greatly contribute the spread of medical CAD/CAM systems.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, advantages and features of the present invention will become more fully understood from the detailed description given hereinafter and the appended drawings which are given by way of illustration only, and thus are not intended as a definition of the limits of the present invention, and wherein.

DESCRIPTION OF THE PREFERRED EMBODIMENT

Figure 1:
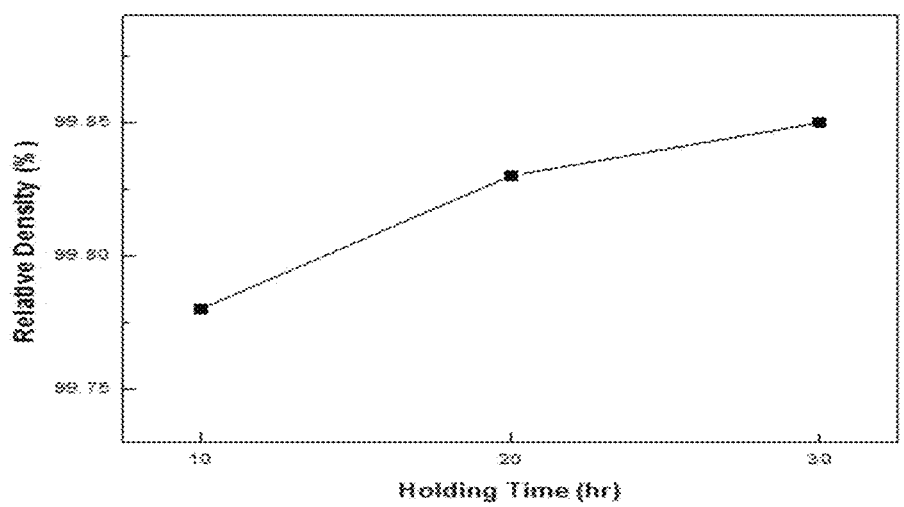
FIG. 1 is a graph of a change in density with a retention time in a sintering process for a machinable zirconia according to the present invention.
Figure 2A:
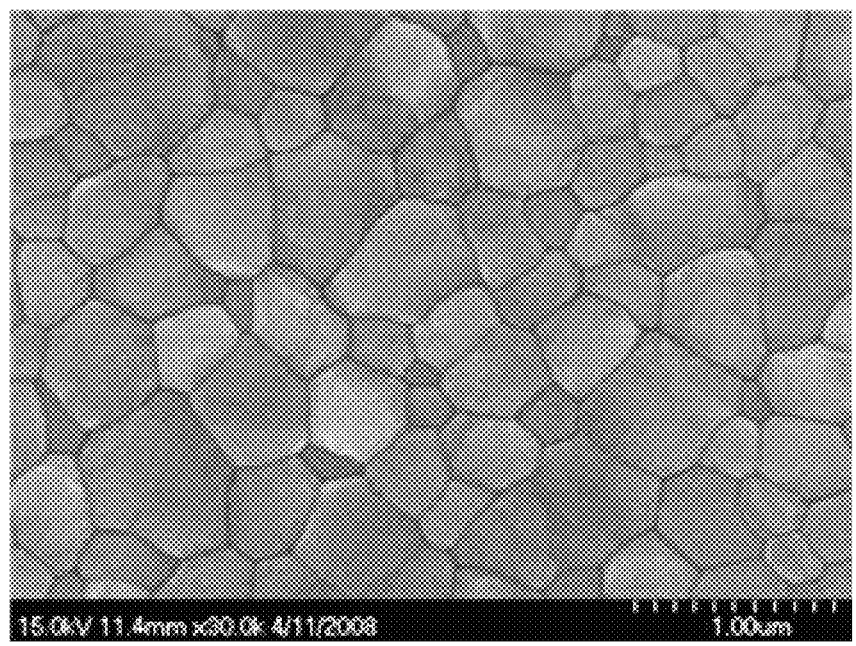
FIGS. 2A to 2D are pictures of microstructures of a commercialized zirconia and a machinable zirconia according to the present invention according to sintering conditions.
Figure 2B:
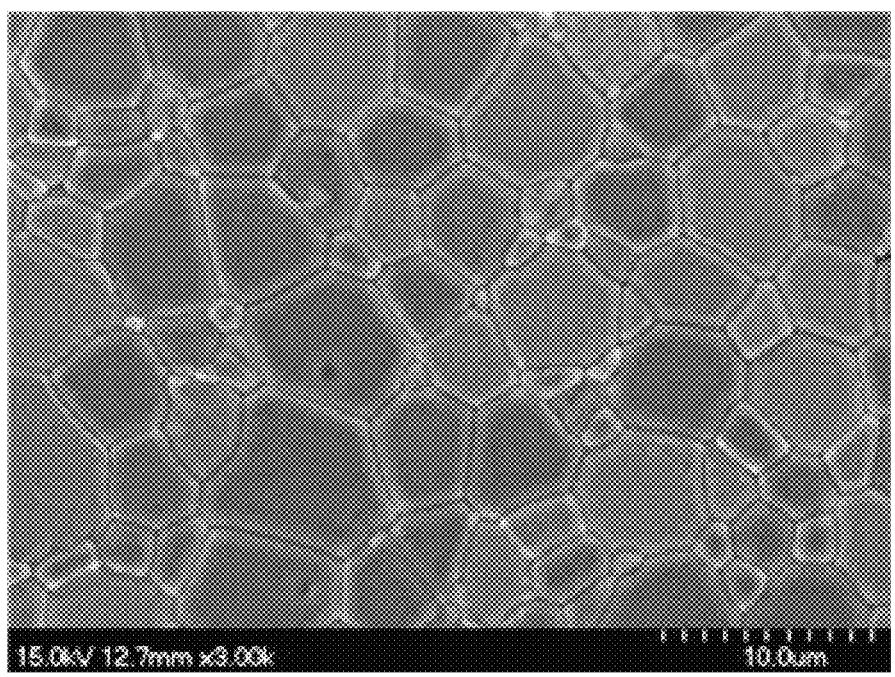
Figure 2C:
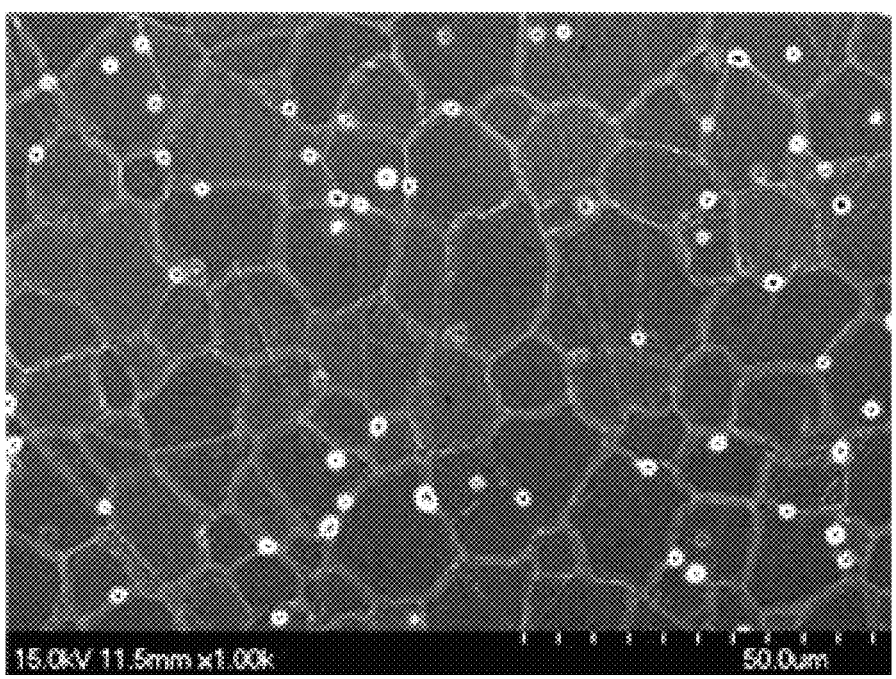
Figure 2D:
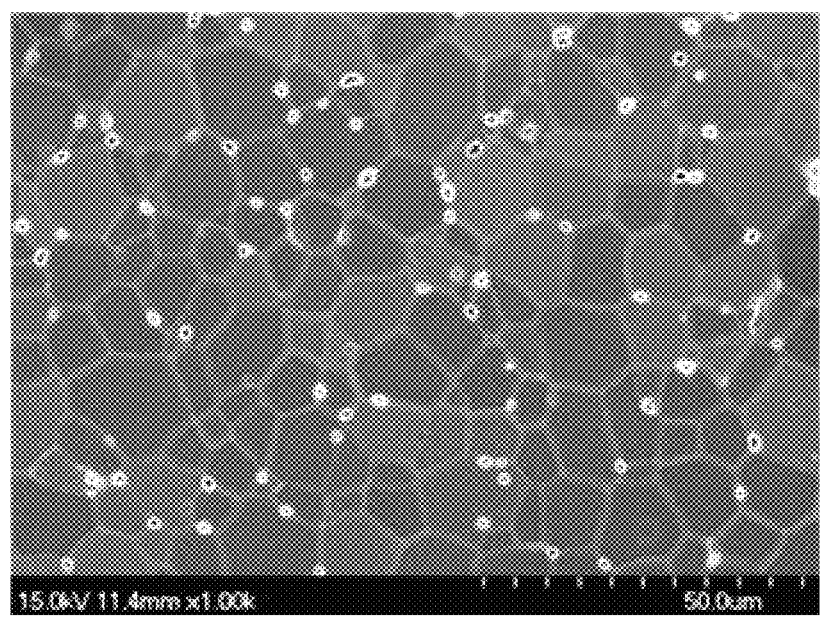

The present invention is to improve machinability by decreasing hardness and increasing fracture toughness by controlling a grain size of a zirconia sintered body and to increase translucency by HIP.

The machinability denotes relative difficulty or easiness in removing a portion of an original material when manufacturing a product by machining the original material. Ceramic machining is practically available only in the case of a porous material such as a zirconia brick. In the case of a high density material such as an alumina or a zirconia, since the hardness is high, during the machining, cracks propagate, and the material is easily destructed.

Therefore, it is difficult to machine the material in an intended shape. In order to machine a ceramic sintered body with a drill made of, for example, tungsten carbide (WC), the ceramic sintered body has low hardness and high fracture toughness so that cracks formed during machining can be controlled not to propagate.

Since the machinability of the ceramic is caused by a chipping process, fracture in the ceramic machining needs to be localized to periphery of a grinding material by a crack deflection mechanism. For the easiness of the chipping, the hardness of the ceramic needs to be low, and due to the high fracture toughness, crack growing needs to be securely localized. Therefore, the ceramic needs have an R-curve behavior where the fracture toughness of the ceramic is gradually increased with increasing crack length. By doing so, low fracture toughness in a short-crack state induces desorption of fine cracks and microstructures during the machining, so that it is possible to obtain high machinability. With respect to high fracture toughness in a long-crack state, the growth of the fine cracks up to a critical crack size which leads to the destruction is suppressed so that the occurrence of brittle fracture is prevented.

In the present invention, in order to improve the machinability of the zirconia, $Nb_2O_5$ or $Ta_2O_5$ is additionally added to $Y_2O_3$ which is added to a zirconia of the related art, so that fracture toughness is maximized and microstructures are coarsened so as to minimize the hardness. In addition, the sintering density is maximized by adding an appropriate oxide and employing HIP, so that it is possible to realize beauty of natural teeth.

In the present invention, in order to optimize the sintering density of the zirconia sintered body and increase an average grain size, the sintering is controlled so that the growth of the grain boundary is facilitated. More specifically, in the present invention, in order to increase the grain size of the zirconia sintered body, the second-step sintering process is performed as described later. Before the temperature is increased from a temperature of the first step up to a temperature of the second step, a retention temperature is retained for a predetermined time, so that it is possible to obtain the zirconia having a high density and a small grain size. In addition, after the sintering step, hot isotropic pressing is additionally performed in a temperature range of 1300 to 1700° C. with a pressure of 10000 to 50000 psi, so that it is possible to further improve physical properties.

On the other hand, the sintering density is retained so that the decrease in hardness does not lead to an excessive decrease in strength or fracture toughness. Therefore, nano particles are used as a raw material of the zirconia sintered body, so that it is possible to obtain a sintering density of 99% or more. A nano-sized oxide is added, so that it is possible to decrease the hardness so as to facilitate the machining. In addition, the strength of the sintered body is set to be in a range of 400 to 1000 MPa, and the fracture toughness of the sintering density is set to be in a range of 9 to 14 MPa·m$^{1/2}$, so that it is possible to maintain excellent mechanical properties while the hardness is decreased down to 8 GPa or less.

As a raw material used for the machinable zirconia according to the present invention, a tetragonal zirconia composite powder containing 79.8 to 92 mol % $ZrO_2$, 4.5 to 10.2 mol % $Y_2O_3$, and 3.5 to 7.5 mol % $Nb_2O_5$, or 5.5 to 10.0 mol % $Ta_2O_5$ may be used. In addition, in order to improve the machinability, an oxide additive may be further contained as described below. In addition, if necessary, in order to improve beauty, a small amount of $F_2O_3$, $Er_2O_3$, $Tb_4O_7$, $Pr_2O_3$, or combination thereof may be additionally contained in range of 0.005 to 5 wt %.

In the case of a pure zirconia, it is known that, during cooling at a high temperature, a cubic phase is stable in a temperature range of the zirconia melting point to about 2370° C., a tetragonal phase is stable in a temperature range of about 2370° C. to about 1170° C., and a monoclinic phase is stable in a temperature range of 1170° C. or less. With respect to the pure zirconia, in the case of cooling the tetragonal phase thereof from a high temperature of 1170° C. or more, the phase transforms into a monoclinic phase at a temperature of 950° C., and the volume is expanded 3 to 5%. Therefore, cracks occur in the entire sintered body. Accordingly, the pure zirconia is unsuitable as a transplant material for a living body used for a hard tissue.

In the present invention, in order to prevent martensitic phase transition of the zirconia, besides $Y_2O_3$, $Nb_2O_5$ or $Ta_2O_5$ is additionally added as a tetragonal-phase stabilizer, so that the tetragonal phase which is sintered at a high temperature of 1170° C. or more is stabilized at a room temperature. In addition, in the case where an yttria-stabilized zirconia (Y-TZP) is exposed in a temperature range of 100 to 300° C. for a long time, the phase transformation from the tetragonal phase to the monoclinic phase and cracks occur, so that the strength is greatly decreased. This is so-called low temperature deterioration phenomenon, which can be prevented by additionally adding $Nb_2O_5$ or $Ta_2O_5$. In the case of containing $Nb_2O_5$, the composition of the machinable zirconia preferably contains 85.6 to 92 mol % $ZrO_2$, 4.5 to 7.5 mol % $Y_2O_3$, and 3.5 to 7.5 mol % of $Nb_2O_5$. In the case of containing $Ta_2O_5$, the composition of the machinable zirconia preferably 79.8 to 88.5 mol % $ZrO_2$, 6.0 to 10.2 mol % $Y_2O_3$, and 5.5 to 10.0 mol % $Ta_2O_5$.

In this manner, the machinable zirconia can improve mechanical properties such as fracture toughness and strength of the tetragonal zirconia and achieve the phase stability of the zirconia, so that it is possible to increase the lifetime of the zirconia for dental products. Particularly, the above-described composition is selected among the composition range where a tetragonal zirconia (non-transformable tetragonal zirconia) exists and low temperature degradation does not occur so that mechanical properties are optimized.

[Sintering Process]

In the present invention, for densification and a fine grain size, a machinable zirconia is sintered in two steps. Namely, after increasing up to a temperature of a first step, the resulting product is retained at a retention temperature for a predetermined time. Next, after the temperature is increased up to a temperature of a second step, sintering is performed.

It is determined that, in the sintering of the second step, after the temperature is increased up to the temperature of the first step, the retention temperature is in a temperature range of about 1350° C. or more so that the density is 75% or more of a theoretical density after the sintering at the temperature. Therefore, the temperature of the first step is determined to be in a temperature range of 1400 to 1600° C. In addition, the temperature of the second step is determined in a temperature range of 1500 to 1700° C. In the embodiment of the present invention, the temperature of the second step is fixed at 1650° C., and the time is adjusted to be 2 hours and 20 hours according to test condition.

TABLE 1

| Temperature of First Step (° C.) | Maintaining Temperature (° C.) | Density (%) |
|---|---|---|
| None | None | 99.51 |
| 1400 | 1300 | 99.60 |
| 1400 | 1350 | 99.59 |
| 1450 | 1350 | 99.60 |
| 1500 | 1450 | 99.77 |
| 1550 | 1450 | 99.85 |
| 1550 | 1500 | 99.70 |
| 1600 | 1450 | 99.68 |

As seen from Table 1, it can be understood that, in the two step sintering processes of the machinable zirconia, the influence of the retention temperature on the density is larger than that of the primary temperature. It is considered that the grain size after final sintering is almost determined at the primary sintering temperature, and the temperature lower than the above-described temperature is retained for a long time in the state where microstructures are fixed, so that the materials are densified while maintaining a desired grain size. Accordingly, the densification occurs. As a result of the test, the primary sintering temperature of 1550° C. is suitable, and in the case where the retention temperature is 1450° C., the optimization can be achieved. In this case, when the sintering is performed in a temperature range of 1650° C. for 2 hours, the density of about 99.85% of the theoretical density is obtained. In order to further shorten the process time by shortening the retention time of hours at a temperature of 1450° C. which is an optimal retention temperature, all the conditions are set to be equal, and the retention time is set to be different as 10 hours, 20 hours, and 30 hours. The comparison of the density is illustrated in FIG. 1.

In the case where the retention time is 30 hours, the highest density is obtained, and in the case where the retention time is 20 hours, there is almost no difference in density. However, in the case where the retention time is 10 hours, during the retention, the density is decreased. By taking into consideration a long time spent between processes, it is determined that the retention time is preferably 20 hours. In order to maximize the sintering density, the sintering is performed as a combination of the densification process where a temperature of 1100° C. is additionally retained to rearrange particles at a low temperature and the two step sintering processes. The result is listed in Table 2. In the second-step sintering process, the temperature of the first step is set to 1550° C., the retention temperature is set to 1450° C., and after the retention for 20 hours, the sintering is performed at the second-step sintering temperature of 1650° C. for 2 hours and for 20 hours, respectively.

TABLE 2

| 1100° C. Retention | 1450° C. Retention Time (hr) | Second Step 1650° C. retention time (hr) | Density (%) |
|---|---|---|---|
| X | 20 | 2 | 99.85 |
| ○ | 20 | 2 | 99.86 |
| X | 0 | 2 | 99.51 |
| ○ | 20 | 20 | 99.78 |
| X | 30 | 20 | 99.65 |
| X | 0 | 20 | 99.41 |

In the case of the second-step retention temperature of 1650° C. and the retention time of 2 hours, the effect of the retention at 1100° C. is very small. However, in the case of the second-step retention temperature of 1650° C. and the retention time of 20 hours, although the retention time is shortened, the density is increased 0.1% or more.

In the sintering of the machinable zirconia, while increasing the retention time at 1650° C., a change in physical properties is observed. The result of observation is listed in Table 3. In the case where the retention time is increased from 20 hours to 40 hours, the density is not improved, but the strength and the hardness are increased.

TABLE 3

| Sintering Time | Density (%) | Strength (MPa) | Hardness (GPa) |
|---|---|---|---|
| 1650° C., 20 hours | 99.39 | 580 | 8.79 |
| 1650° C., 40 hours | 99.39 | 637 | 9.29 |

A general 3Y-TZP and the machinable zirconia according to the present invention which are sintered at 1500° C. for 2 hours are sintered at 1650° C. for 2 hours, 20 hours, and 40 hours. The results are shown in FIGS. 2A to 2D. The machinable zirconia which is sintered for 40 hours shows that the grain boundaries do not maintain a straight line shape. This is because the secondary phase occurs due to dispersion of ions of additives for a long time at the grain boundaries where ion concentration of the additives is increased due to the long time sintering. If the grains do not maintain a straight line shape, an effect of dispersion of external stress occurs. Therefore, it is considered that, without an increase in density, the strength and the hardness are increased.

[Oxide Additive]

[a. Machinable Zirconia Added with $TiO_2$]

$ZrO_2$ powder (KZ-0Y, Kyoritsu), $Y_2O_3$ (Uranos Chem.), and $Nb_2O_5$ are mixed with the above-described composition ratio, and ball milling is performed for 24 hours. After drying the resulting product, the mixture powder is calcinated. By performing attrition milling for 3 hours by using a zirconia ball, the powder of which size is increased during the calcination process is ground to obtain a fine compound. By drying the powder again and sieving with a 125 mesh of sieve, a machinable zirconia powder ((Y, Nb)-TZP) is prepared.

For spray drying, it is necessary to manufacture slurry which has good dispersibility and is stable. The slurry utilizes water as a solvent, and the amount thereof is in a range of 20 to 50 wt %. In order to obtain the slurry which has good dispersibility and is stable, a binder, a dispersant, a plasticizer, and the like are added. In order to manufacture the slurry for the spray drying, a nano-sized oxide is added to the machinable zirconia powder manufactured in advance.

1.2 wt % of a dispersant (Duramax D-3005) is added to a distilled water, and ball milling is performed for 24 hours, so that the nano-sized oxide is dispersed. The zirconia powder and the distilled water is mixed at a ratio of 100:70, and 1.2 wt % of the dispersant is added thereto. Next, ball milling is performed for one hour, so that the zirconia powder is dispersed. Next, an oxide additive which is separately dispersed for 24 hours is added, and dispersing is performed for one hour again. A binder (PEO 0.24 wt %, PVP 0.08 wt %, PVA 0.08 wt %) and a plasticizer (glycerol) are added to the dispersed slurry, and milling is performed for 2 hours. Next, an anti-foaming agent and a lubricant (Ceramic Lubricant, produced by San NOPCO) are added, and milling is further performed for 30 minutes. As a result, the slurry is completed.

The prepared slurry is supplied to an atomizer which rotates at a high speed, and spray drying is performed, so that spherical granules are obtained. The granules of the machinable zirconia are inserted into a mold, and compression pressing is performed. All specimens are subjected to uniaxial pressing in a 20φ mold with a molding pressure of 1.5 tons, and after that, cold isostatic pressing (CIP) is performed at a pressure of 200 MPa.

Figure 3:
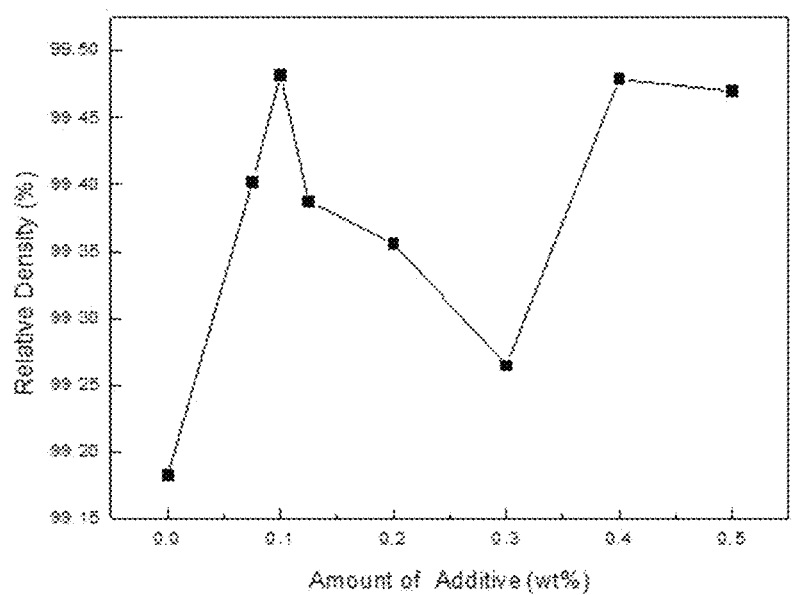
FIG. 3 is a graph illustrating a result of change in density of a machinable zirconia according to an amount of an oxide additive.

As a nano-sized oxide, 0 to 0.5 wt % $TiO_2$ is added to the machinable zirconia powder, and sintering is performed at 1650° C. for 2 hours. A result of a change in density according to an amount of the additive is illustrated in FIG. 3. When 0.1 wt % of an oxide additive is added, the sintering density is changed from 98.87% to 99.48%. The effect of high improvement of density is obtained.

A power where 0.1 wt % $TiO_2$ is added to the machinable zirconia is sintered at 1650° C. for 20 hours. The comparison of physical properties between the powder and the specimens where no additive is added is listed in Table 4.

TABLE 4

| | Machinable Zirconia | Machinable Zirconia + Additive $TiO_2$ |
|---|---|---|
| Density (%) | 99.39 | 99.41 |
| Strength (MPa) | 546 | 580 |
| Hardness (GPa) | 8.76 | 8.79 |

In the case of 20-hour sintering, although the density is not improved in comparison to the 2-hour sintering, the strength is increased, and the hardness is hardly affected. The hardness of the specimen which is sintered for 20 hours is remarkably low in comparison to a zirconia (13.2 GPa) currently used for CAD/CAM dentistry.

In order to compare to a ceramic for dental products of the related art, a commercial 3Y-TZP specimen (3YSB-E, Tosoh) which is sintered at 1500° C. for 2 hours, a dental glass ceramic (IPS e.max, Ivoclar) which is subjected to thermal treatment at 850° C., a specimen where the machinable zirconia according to the present invention added with $TiO_2$ which is sintered at 1650° C. for 20 hours are surface-grinded. Next, thermal treatment is performed at 1200° C. for 2 hours, so that residual stress of the surface generated during the surface grinding is removed.

Figure 4A:
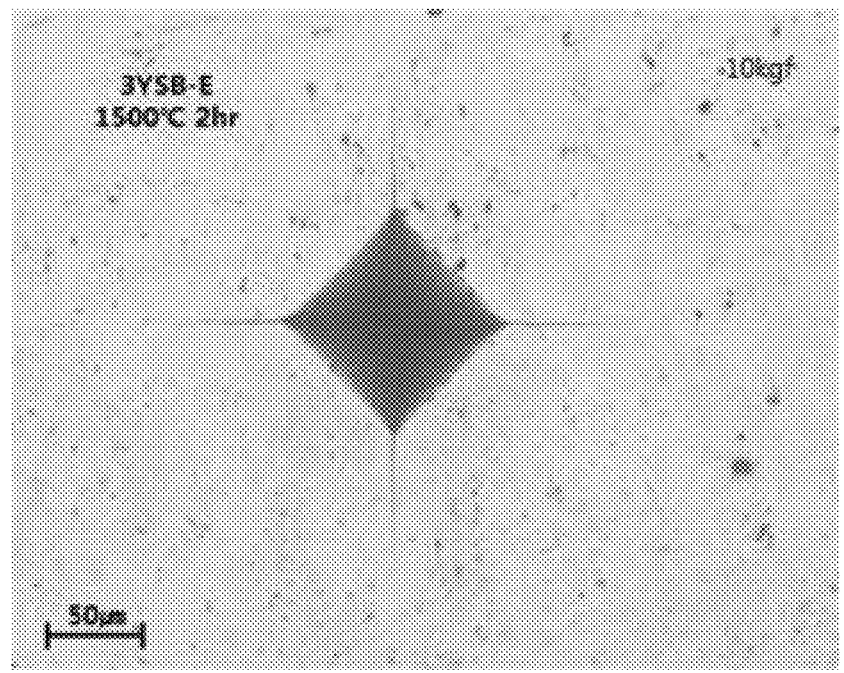
FIGS. 4A to 4C are pictures illustrating a result of hardness test of a commercialized ceramic for dental products and the machinable zirconia.
Figure 4B:
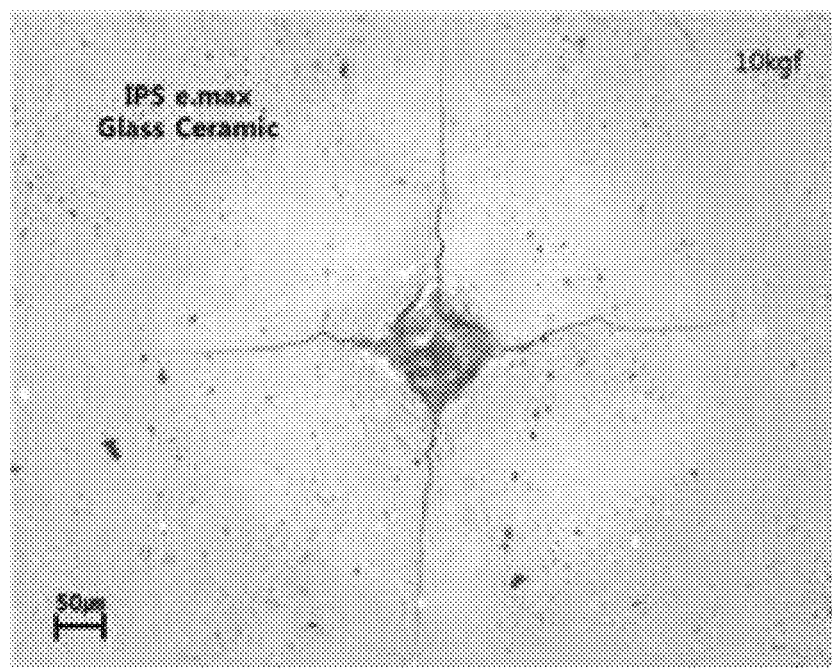
Figure 4C:
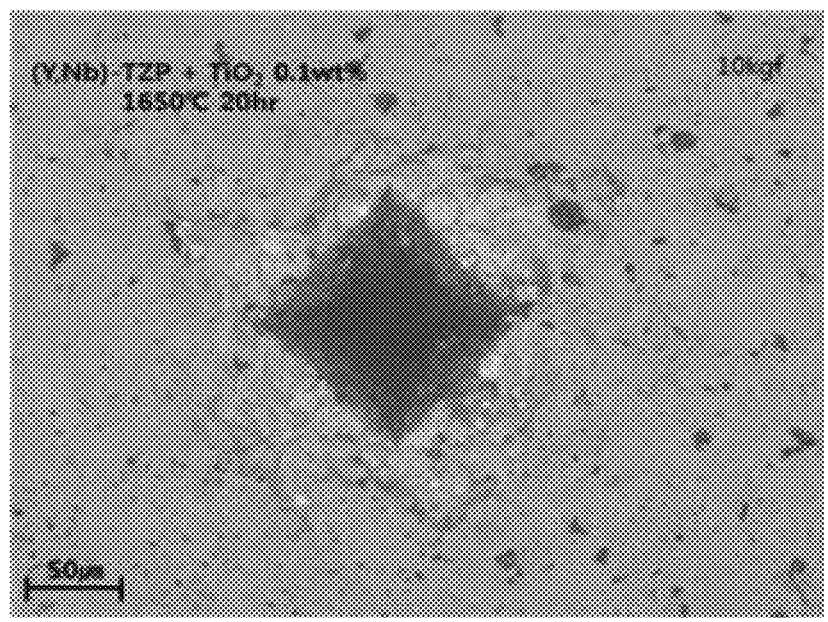
Figure 5:
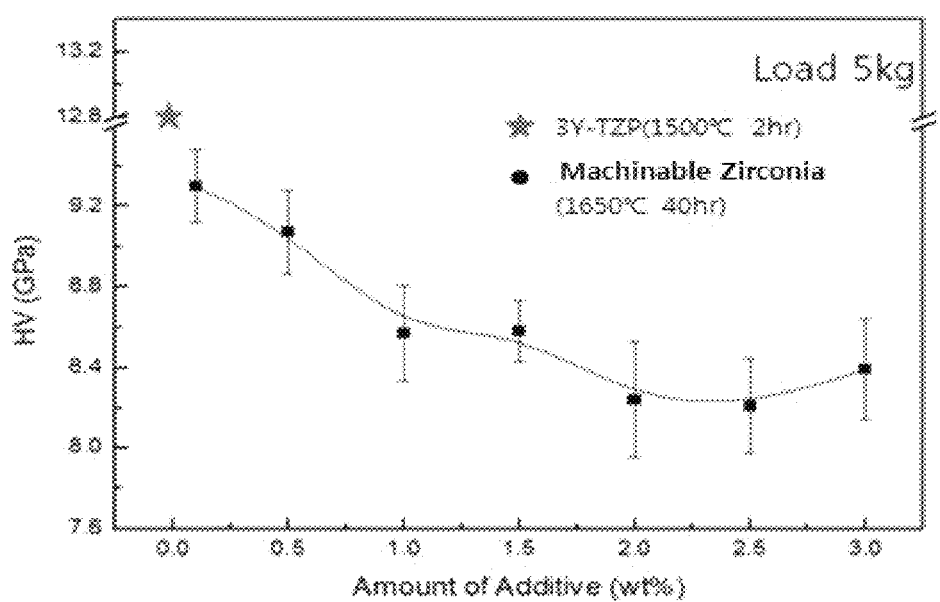
FIG. 5 is a graph illustrating a change in hardness of the machinable zirconia according to an amount of an additive $TiO_2$.
Figure 6:
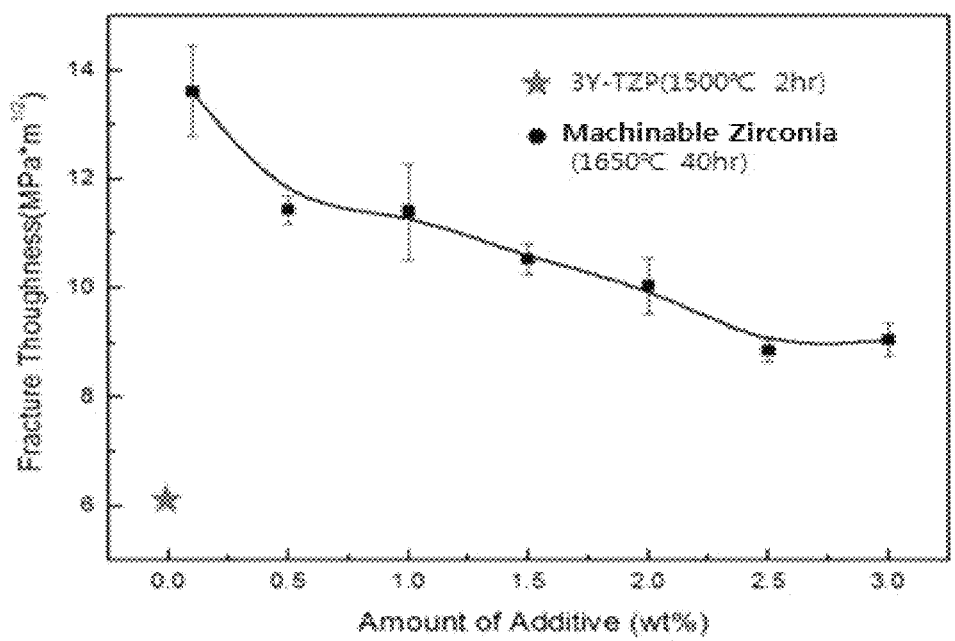
FIG. 6 is a graph illustrating a change in fracture toughness of the machinable zirconia according to an amount of the additive $TiO_2$.

Next, results of response on indentation with the same load are compared. Indentations are left on the grinded surface by using a diamond indenter with a load of 10 kgf, and crack formation is observed. As illustrated in FIGS. 4A to 4C, in the case of the machinable zirconia, unlike the ceramic for dental products of the related art, due to high fracture toughness, no cracks propagate from the corners of the indent. The hardness and fracture toughness are used as physical property variables for optimization of the machinability, and the composition where the hardness is minimized or the fracture toughness is maximized is demonstrated. The zirconia powder previously formed is added with the oxide additive $TiO_2$ of which amount is changed in a range of 0.5 to 3.0 wt %, and the sintering is performed at a temperature of 1650° C. for 40 hours, so that the specimens are manufactured. A result of the observation of a change in hardness of the specimens is illustrated in FIG. 5. In the case where a commercial 3Y-TZP (3YSB-E, Tosoh, Japan) is sintered at a temperature of 1500° C. for 2 hours, the hardness is about 13.2 GPa. On the contrary, in the case where the machinable zirconia according to the present invention is added with the oxide additive of which amount is changed in a range of 0.1 to 3.0 wt %, the hardness is gradually decreased down to the hardness of the case of the amount of additive being 2.5 wt %. When the amount of the oxide additive is 2.5 wt %, the hardness has the lowest value of 8.2 GPa. The change in fracture toughness also has a tendency of being coincident with the change in hardness as illustrated in the result of FIG. 6. From the result, with respect to the machinable zirconia according to the present invention, in order to minimize the hardness and to maximize the fracture toughness, the amount of the oxide additive is determined to be in a range of 0.5 to 2.5 wt %, preferably, in a range of 1.0 to 2.0 wt %.

Figure 7:
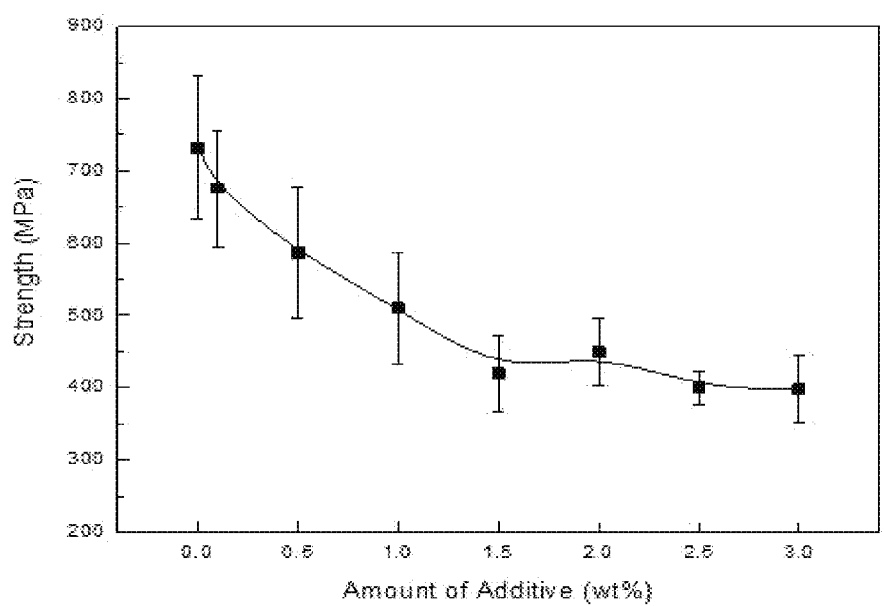
FIG. 7 is a graph illustrating a change in strength of the machinable zirconia according to an amount of the additive $TiO_2$.

It is observed that, as the amount of the oxide additive is increased, the grain size of the machinable zirconia added with the oxide is increased, and the strength is decreased as illustrated in the result of FIG. 7. However, in the case where the amount of the additive is in a range of 1.0 to 2.0 wt %, a biaxial flexural strength is higher than 400 MPa. Therefore, it is considered that the machinable zirconia has such physical properties that the machinable zirconia can be safely applied to a molar tooth part or a 3-unit bridge.

[b. Addition of $CeO_2$]

Figure 8A:
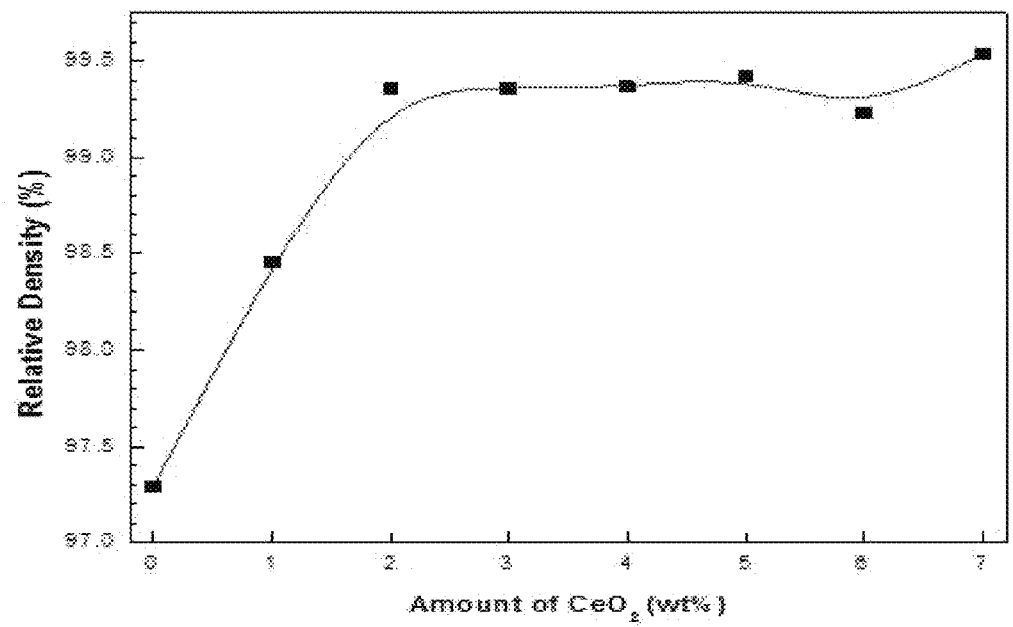
FIGS. 8A and 8B are graphs illustrating a change in density and a change in hardness according to an amount of an additive $CeO_2$.
Figure 8B:
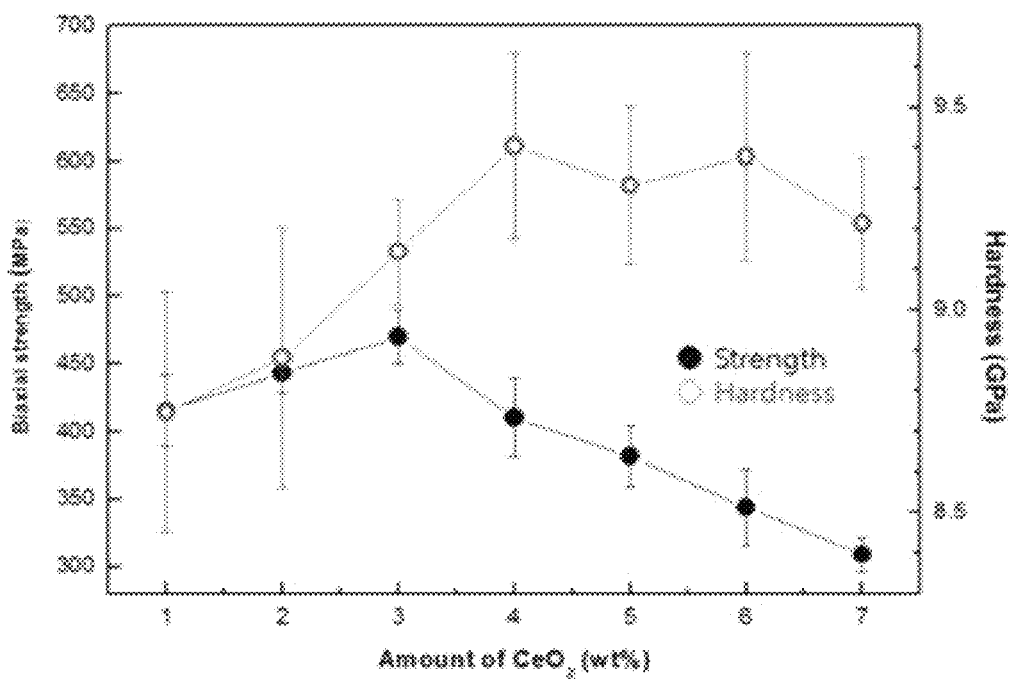

An additive $CeO_2$ which is synthesized by a hydrothermal synthesis method is added to the machinable zirconia powder, and pressing and sintering are performed by using the same methods as those of the above-described embodiment. The change in physical properties is observed. With respect to the specimens where the amount of the additive $CeO_2$ is changed in a range of 1 to 7 wt %, the change in density and the change in hardness are illustrated in FIGS. 8A and 8B. The density is increased up to 99.5% until the amount of additive $CeO_2$ is increased up to 2 wt %. Although the amount of the additive is further increased, the density is not changed. On the other hand, the strength is gradually increased until the amount of the additive is increased up to about wt %. As the amount of the additive is further increased, the strength is linearly decreased according to the amount of the additive $CeO_2$. It is considered that, during the fracture, $CeO_2$ as a stabilizer suppresses phase transition from the tetragonal phase to the monoclinic phase, so that the fracture toughness is decreased. Therefore, according to the linear fracture mechanics, it is considered that the strength is proportionally decreased. Furthermore, addition of $CeO_2$ leads to an increase in grain size of the zirconia. Therefore, in this case, it is considered that the strength is decreased according to the coarsening of the grains. It is observed that the hardness is constantly increased from 8.7 GPa to 9.4 GPa until the amount of the additive is 4 wt %, and as the amount of the additive is further increased, the hardness is gradually decreased. This denotes that the addition of $CeO_2$ up to 4 wt % has an effect of reducing the deformation of the present invention during the indentation. On the other hand, it is observed that, when the amount of the additive $CeO_2$ is 3 wt % or more, the strength is decreased, and as the amount of the additive is increased to be 3 wt % or more, the color of the specimens is increasingly dark.

[c. Co-addition of $TiO_2$ and $CeO_2$]

Figure 9A:
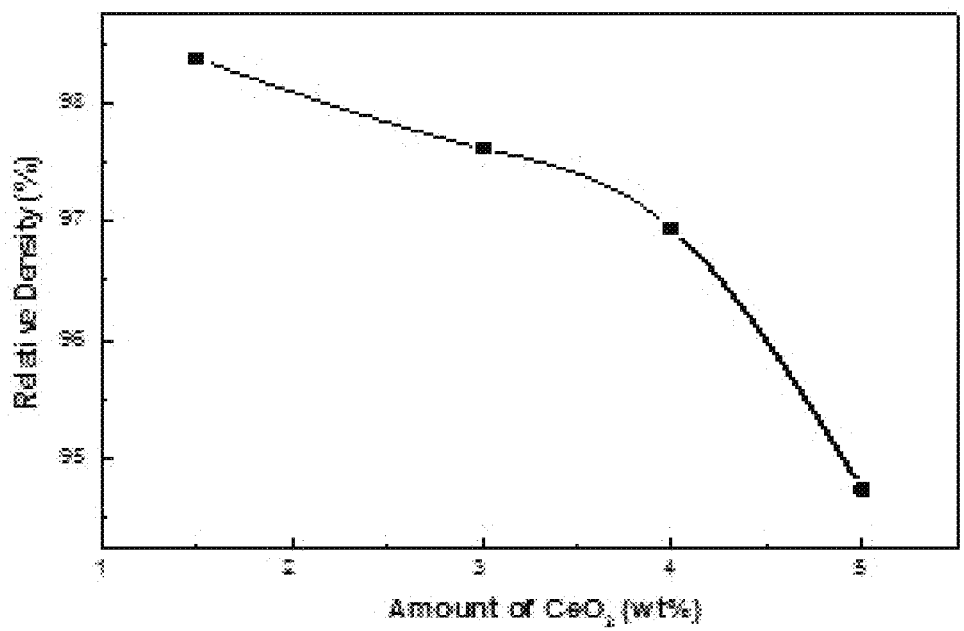
FIGS. 9A and 9B are graphs illustrating a change in density and a change in hardness according to an amount of the additive $TiO_2$ and an amount of the additive $CeO_2$.
Figure 9B:
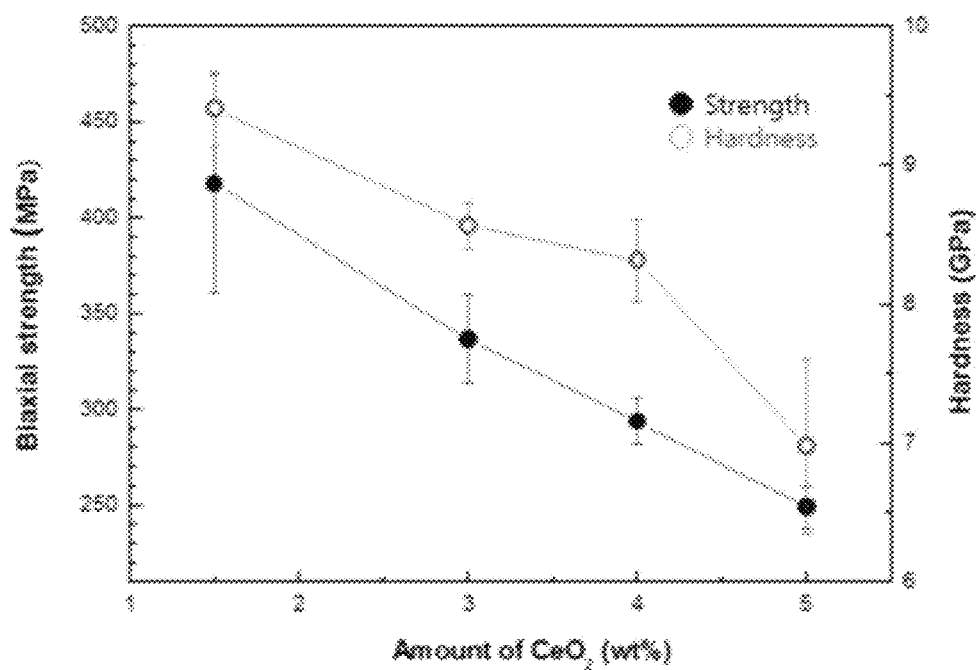

The specimens are prepared by adding the amount of the additive $TiO_2$ which is fixed at 2 wt % and the amount of the additive $CeO_2$ which is changed in a range of 1.5 to 5 wt % to the machinable zirconia powder. Change in physical properties is observed. The change in density and the change in strength and hardness according to the amounts of the additives are illustrated in FIGS. 9A and 9B. In the case where the amount of the additive $TiO_2$ is fixed and the amount of the additive $CeO_2$ is changed, all of the density, the strength, and the hardness have a tendency of being decreased in inverse proportion to the amount of the additive $CeO_2$.

As the amount of the additive $CeO_2$ is increased, the strength and the hardness are almost linearly decreased. It is considered that this is because of the influence of $TiO_2$. In addition, it is considered that addition of both of $TiO_2$ and $CeO_2$ is greatly contributed to the coarsening of the zirconia.

[d. Addition of $SiO_2$]

Figure 10:
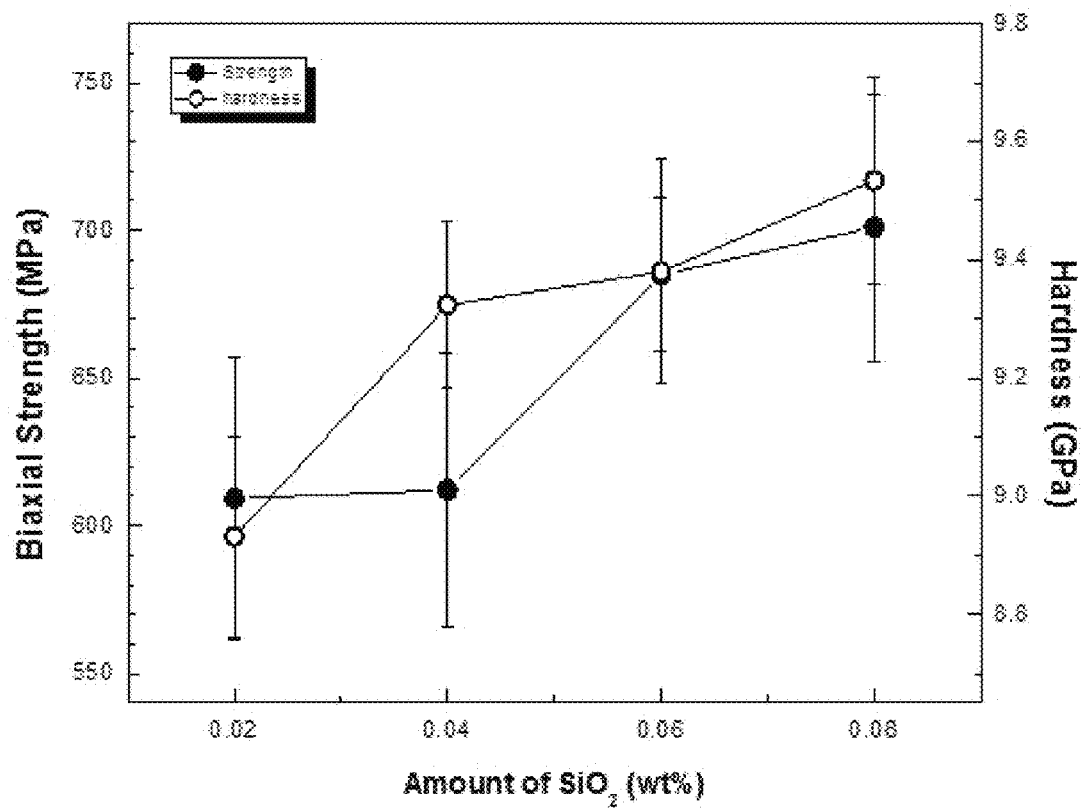
FIG. 10 is a graph illustrating a change in density and a change in hardness according to an amount of an additive $SiO_2$.

In the test of addition of both of $TiO_2$ and $CeO_2$, in the case where the hardness is decreased, both of the density and the strength are decreased. Therefore, in order to compensate for this, a small amount of $SiO_2$ is added to the machinable zirconia powder. The change in density and hardness is observed. The density of the zirconia added with $TiO_2$ and $CeO_2$ is increased when 0.02 wt % $SiO_2$ is added. Until the amount of the additive $SiO_2$ is 0.08 wt %, the increased density is generally maintained. As a result of measurement of the strength and the hardness of the specimens where $SiO_2$ is added up to 0.08 wt %, as illustrated in FIG. 10, the strength is remarkably increased, and the hardness is gradually increased. As a result, it is considered that enhancement occurs by coating the zirconia grain boundaries with a small amount of glass phase.

[Machinability Test]

The zirconia powder added with 1 to 2 wt % $TiO_2$ which has a strength of 400 MPa or more and low hardness is sintered at a temperature of 1650° C. for 40 hours, so that zirconia blocks for machinability test are manufactured. A diamond drill having a diameter of 3 mm is mounted on a machining instrument (Mynx 400, Daewoo, Korea). While supplying a cutting oil, the machining is performed. The rotation speed of the drill of the instrument is fixed at 5000 rpm, the feed speed is fixed at 18 mm/sec, and the depth of cutting is fixed at 0.15 mm. The machinability is determined by machining the specimen from the surface of the specimen down to the depth of 6 mm and by measuring a time taken to perform the machining. Table 5 lists average time taken for a 3 mm drill to machine the depth of 6 mm.

TABLE 5

| Specimen Type | Addition of 1.0 wt % Oxide | Addition of 1.5 wt % Oxide | Addition of 2.0 wt % Oxide | 3Y-TZP |
|---|---|---|---|---|
| Average Machining Time (sec) | 50.7 | 52.5 | 50.8 | Machining Is Impossible |
| Machining Speed (mm/sec) | 0.12 | 0.11 | 0.12 | — |

Figure 11A:
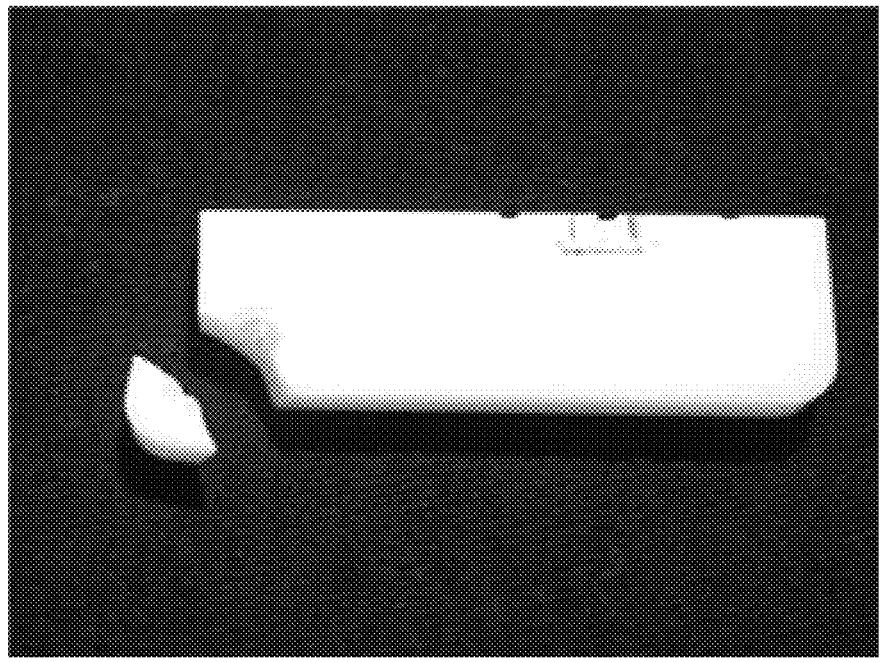
FIGS. 11A and 11B are pictures illustrating a result of machining test for a commercialized zirconia and the machinable zirconia according to the present invention.
Figure 11B:
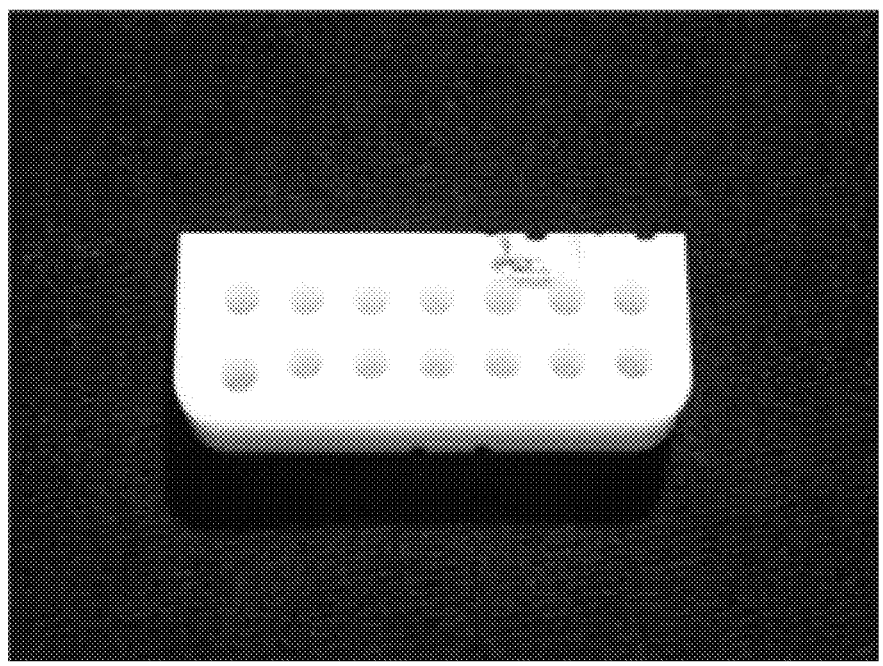

All the specimens added with the oxide additive in a range of 1 to 2 wt % can be machined at a machining speed of 0.1 mm/sec or more. When the amount of the additive is 1.0 wt %, the most excellent machining speed is observed. On the contrary, in the case of a fully sintered body of general 3Y-TZP, as illustrated in FIG. 11A, because of higher hardness and lower fracture toughness than those of the machinable zirconia, in the same conditions, a diamond drill is destructed during the machining, and the machining of holes having a diameter of 3 mm cannot be achieved. In addition, because of the low fracture toughness, brittle fracture of the specimen itself is also observed. However, the machining of the machinable zirconia according to the present invention is completed without the occurrence of brittle fracture (FIG. 11B).

It is considered that a difference in machinability between the machinable zirconia according to the present invention and the fully sintered body of the commercial 3Y-TZP is caused by the hardness and the fracture toughness. Namely, in the case of the machinable zirconia added with 1 to 2 wt % additive, a brittle index $H/K_{IC}$ has a low value in a range of 0.75 to 0.82. However, in the case of the 3Y-TZP, the brittle index has a high value of 2.2, it is considered that the machining is impossible in the same conditions.

[Translucency]

Figure 12:
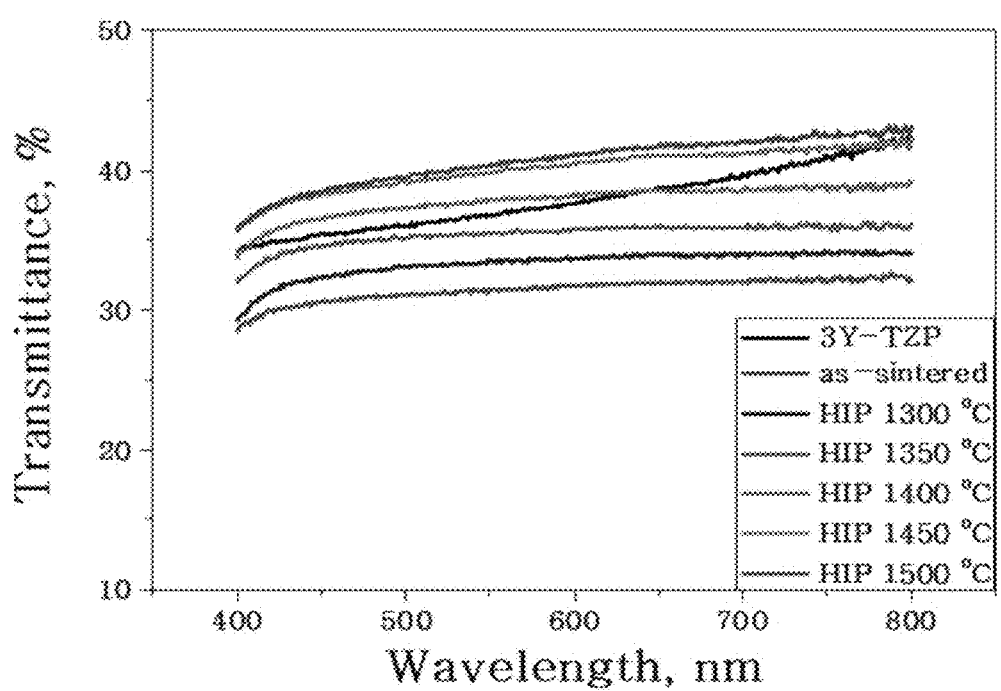
FIG. 12 is a graph illustrating the effect of hot isostatic pressing temperatures on visible light transmittance of a claimed zirconia. The translucency was compared with those of the zirconia sintered conventionally only (as-sintered) and the current dental zirconia (3Y-TZP).

Translucency is one of critical requirements for dental restoration ceramics besides mechanical properties. The translucency of zirconia of the present invention was significantly improved by using hot isostatic press (HIP) after the conventional sintering in air as shown in FIG. 12. The result demonstrates that the translucency of the present zirconia, whose composition is 90.6 mol % $ZrO_2$—5.3 mol % $Y_2O_3$—4.1 mol % $Nb_2O_5$, was increased up to about 40% after HIP at 1500° C. compared to the specimen only sintered conventionally for 5 h at 1650° C. (as-sintered). The translucency increases in proportion to the HIP temperatures and the values after HIP at temperatures higher than 1450° C. are higher than that of dental zirconia (3Y-TZP) currently employed as restoration material.

Figure 13:
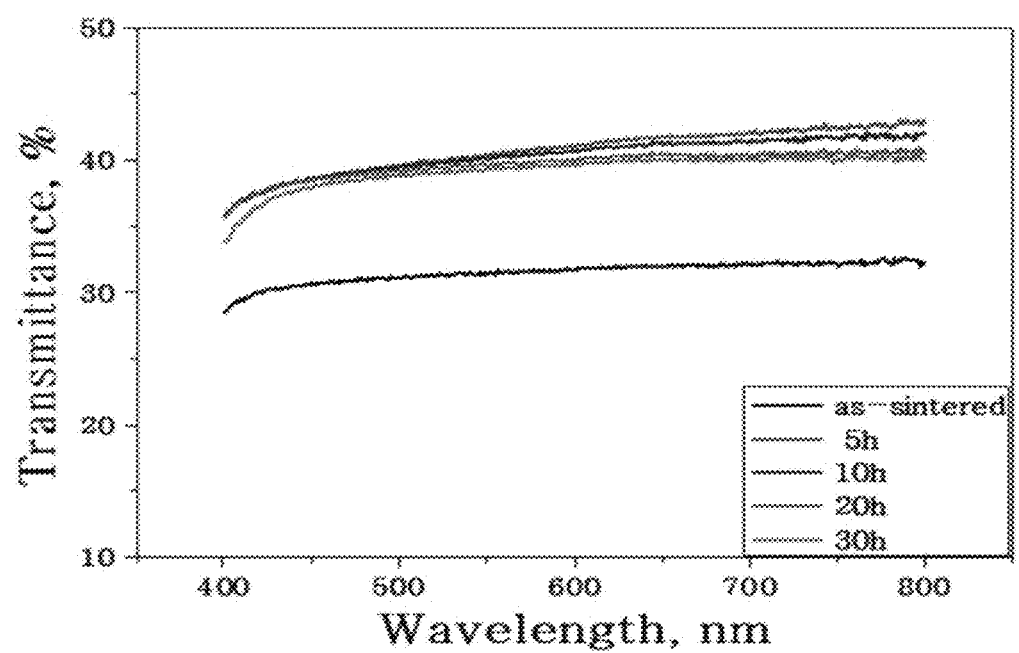
FIG. 13 is a graph illustrating the effect of sintering time during conventional sintering at 1650° C. on visible light transmittance of a claimed zirconia after HIP for 2 hours at 1500° C. The translucency was compared with that of the zirconia sintered conventionally only for 5 hours at 1650° C. (as-sintered).

The translucency of the HIP-treated zirconia depends on conventional sintering parameters prior to HIP. In general the translucency varies inversely with grain size of conventionally sintered zirconia as long as sintered density is higher than 90% of the theoretical density. Since the grain size decreases with decrease in sintering temperature and time, the present zirconia sintered conventionally for 5 h at 1650° C. and then HIP at 1500° C. shows the highest translucency as shown in FIG. 13. However, the machinability and fracture toughness increase with increase in the grain size so that there must be a compensation between the translucency and the machinability by controlling processing parameters involved in the conventional sintering. We believe that HIP at the range of 1400-1700° C. after conventional sintering at 1500-1700° C. results in optimum properties for dental restorations.

With respect to the machinable zirconia of the present invention, a complicated method of manufacturing a prosthesis in a CAD/CAM method of the related art which include a primary sintering (partial sintering) step, a machining step, and a secondary sintering (full sintering) step is simplified into two steps of sintering and machining. Therefore, it is expected that it is possible to reduce the production cost of the prosthesis, and it is possible to greatly contribute the expansion of use of the prosthesis. The machinable zirconia according to the present invention can be effectively applied to various biological transplants as well as prostheses.

While the present invention has been particularly shown and described with reference to exemplary embodiments thereof, it will be understood by those skilled in the art that various changes in form and details may be made therein without departing from the spirit and scope of the invention as defined by the appended claims. The exemplary embodiments should be considered in descriptive sense only and not for purposes of limitation. Therefore, the scope of the invention is defined not by the detailed description of the invention but by the appended claims, and all differences within the scope will be construed as being included in the present invention.

What is claimed is:

1. A machinable zirconia as a sintered body which is formed to include a tetragonal zirconia composite powder containing 79.8 to 92 mol % $ZrO_2$, 4.5 to 10.2 mol % $Y_2O_3$, 3.5 to 7.5 mol % $Nb_2O_5$ or 5.5 to 10.0 mol % $Ta_2O_5$, and a $TiO_2$ nano powder which is added with a weight ratio of between 0.05 wt % and 2.5 wt % of the composite powder,
wherein a density of the sintered body is 99% or more, an average particle diameter of particles of the sintered body is 2 μm or more, hardness of the sintered body is in a range of 4 to 10 GPa, fracture toughness of the sintered body is in a range of 9 to 14 MPa·m$^{1/2}$, and a strength of the sintered body is in a range of 400 to 1000 MPa.

2. The machinable zirconia according to claim 1, wherein the sintered body further contains $CeO_2$ in a range of 0.5 to 3 wt %.

3. The machinable zirconia according to claim 1, wherein the sintered body further contains $SiO_2$ in a range of 0.2 to 0.8 wt %.

4. The machinable zirconia according to claim 1, wherein the sintered body further contains $F_2O_3$, $Er_2O_3$, $Tb_4O_7$, $Pr_2O_3$, or combination thereof in a range of 0.005 to 5 wt %.

5. A method of manufacturing a machinable zirconia, comprising:
preparing a raw material including a tetragonal zirconia composite powder containing 79.8 to 92 mol % $ZrO_2$, 4.5 to 10.2 mol % $Y_2O_3$, 3.5 to 7.5 mol % $Nb_2O_5$ or 5.5 to 10.0 mol % $Ta_2O_5$, and a $TiO_2$ nano powder which is added with a weight ratio of between 0.05 wt % and 2.5 wt % of the composite powder;
forming composite granules by spraying and drying slurry containing the raw material; and
performing sintering after molding the granules,
wherein the sintering is performed in a temperature range of 1500 to 1700° C. for 2 to 40 hours.

6. The method according to claim 5, wherein the sintering includes:
increasing a temperature up to a temperature of 1400 to 1600° C.;
retaining the temperature for a predetermined time; and
increasing the temperature up to a temperature of 1500 to 1700° C.

7. The method according to claim 6, wherein the retaining the temperature is performed in a temperature range of 1300 to 1500° C. for 20 to 30 hours.

8. The method according to claim 6, wherein after the sintering, hot isotropic pressing is additionally performed in a temperature range of 1300 to 1700° C. with a pressure of 10000 to 50000 psi so as to improve translucency.

* * * * *